United States Patent [19]

Jaeggi

[11] Patent Number: 5,036,058
[45] Date of Patent: Jul. 30, 1991

[54] N-SUBSTITUTED AMINOALKANEDIPHOSPHONIC ACIDS

[75] Inventor: Knut A. Jaeggi, Basel, Switzerland
[73] Assignee: Ciba-Geigy Corporation, Ardsley, N.Y.
[21] Appl. No.: 481,482
[22] Filed: Feb. 16, 1990

[30] Foreign Application Priority Data

Mar. 8, 1989 [CH] Switzerland .................. 866/89

[51] Int. Cl.$^5$ ................. A61K 31/675; C07F 9/02
[52] U.S. Cl. ............................. 514/86; 514/79; 514/85; 514/89; 514/92; 514/94; 514/102; 514/107; 544/243; 544/337; 546/22; 546/23; 548/112; 548/119; 562/13; 562/14; 562/21
[58] Field of Search ............... 544/243; 546/21, 22; 548/119, 112; 562/13, 14, 21; 514/85, 86, 88, 89, 92, 94, 107, 79, 102

[56] References Cited

U.S. PATENT DOCUMENTS

| | | | |
|---|---|---|---|
| 4,503,049 | 3/1985 | Biere et al. | 562/13 |
| 4,639,338 | 1/1987 | Stahl et al. | 260/502.5 |
| 4,711,880 | 12/1987 | Stahl et al. | 514/108 |
| 4,732,998 | 3/1988 | Binderup | 562/13 |
| 4,814,326 | 3/1989 | Rosini et al. | 562/13 |
| 4,857,513 | 8/1989 | Oku et al. | 562/13 |
| 4,871,720 | 10/1989 | Jaeggi | 544/243 |
| 4,876,248 | 10/1989 | Breliere et al. | 562/13 |
| 4,933,472 | 6/1990 | Isomura et al. | 562/13 |

FOREIGN PATENT DOCUMENTS

| | | |
|---|---|---|
| 177443 | 4/1986 | European Pat. Off. . |
| 186405 | 7/1986 | European Pat. Off. . |
| 272208 | 6/1988 | European Pat. Off. . |
| 3623397 | 1/1988 | Fed. Rep. of Germany . |
| 00829 | 2/1988 | World Int. Prop. O. . |

*Primary Examiner*—Cecilia Shen
*Attorney, Agent, or Firm*—JoAnn Villamizar

[57] ABSTRACT

Compounds of the formula I

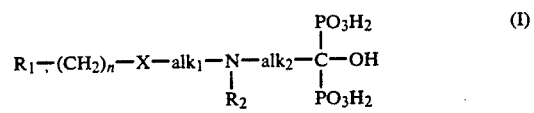

in which $R_1$ is an aromatic radical, n is 0, 1, 2 or 3, X is an oxy group, a thio group which can be oxidized or an imino group which is unsubstituted or has aliphatic substituents, $alk_1$ and $alk_2$ are identical or different divalent aliphatic radicals, and $R_2$ is hydrogen or a monovalent aliphatic radical and salts thereof have properties which regulate calcium metabolism and can be employed for the treatment of diseases connected with disturbances in this metabolism. They are prepared, for example, by reacting a compound of the formula

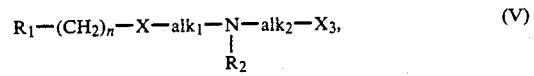

in which $X_3$ is carboxyl with a phosphorylating agent and hydrolysing the primary product.

29 Claims, No Drawings

N-SUBSTITUTED AMINOALKANEDIPHOSPHONIC ACIDS

The invention relates to N-substituted aminoalkanediphosphonic acids of the formula I

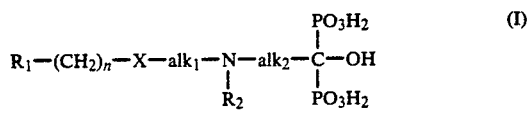

in which $R_1$ is an aromatic radical, n is 0, 1, 2 or 3, X is an oxy group, a thio group which can be oxidized or an imino group which is unsubstituted or has aliphatic substituents, $alk_1$ and $alk_2$ are identical or different divalent aliphatic radicals and $R_2$ is hydrogen or a monovalent aliphatic radical, and to salts thereof, to a process for the preparation of the compounds according to the invention, to pharmaceutical formulations containing the latter and to their use as active compounds for medicaments.

The aromatic radical is, for example, a monocyclic or bicyclic aryl radical, such as a phenyl, naphthyl or indanyl radical, or a hetero aryl radical containing 1 or 2N atoms, 1O or S atom, 1N atom and 1O atom or 1N atom and 1S atom, such as an imidazolyl, thiazolyl, oxazolyl or, in particular, pyridyl, pyrimidinyl or pyridazinyl radical.

The aryl or hetero aryl radicals mentioned can be substituted, such as monosubstituted, disubstituted or trisubstituted, particularly monosubstituted or disubstituted, especially by lower alkyl, lower alkoxy, lower alkylenedioxy, hydroxyl, trifluoromethyl and/or halogen.

Examples of monovalent aliphatic radicals are lower alkyl or lower alkenyl radicals, while examples of divalent aliphatic radicals are lower alkylene radicals.

Thio which can be oxidized is thio, sulfonyl or sulfonyl, in particular thio or sulfonyl.

Examples of imino which is unsubstituted or has aliphatic substituents are $C_1$–$C_4$alkylimino, such as methylimino, ethylimino or propylimino.

In the preceding and following text lower radicals and compounds are to be understood as meaning, for example, radicals and compounds containing up to an including 7, preferably up to and including 4, carbon atoms (C atoms).

Lower alkyl is, for example, $C_1$–$C_7$alkyl, preferably $C_1$–$C_4$alkyl, such as methyl, ethyl, propyl, isobutyl or butyl, but can also be isobutyl, secondary butyl, tertiary butyl or a pentyl, hexyl or heptyl group.

Lower alkenyl is, for example, $C_2$–$C_4$alkenyl, such as vinyl, allyl or but-2-enyl, but can also be a $C_5$–$C_7$alkenyl group, such as pentyl, hexenyl or heptenyl.

Lower alkylene is, for example, $C_1$–$C_7$alkylene, in the case of $alk_1$ especially $C_2$–$C_6$alkylene, such as ethylene, 1,3-propylene, 1,4-butylene or 1,5-pentylene, and, in the case of $alk_2$, especially $C_1$–$C_4$alkylene, such as ethylene, as a secondary choice, methylene or 1,3-propylene.

Lower alkoxy is, for example, $C_1$–$C_7$alkoxy, preferably $C_1$–$C_4$alkoxy, such as methoxy, ethoxy, propoxy, isopropoxy or butoxy, but can also be isobutoxy, secondary butoxy, tertiary butoxy or a pentyloxy, hexyloxy or heptyloxy group.

Lower alkylenedioxy is, for example, methylenedioxy or ethylenedioxy.

Halogen is, for example, a halogen of an atomic number up to and including 35, such as chlorine or fluorine, and also bromine.

Examples of salts of compounds of the formula I are salts thereof with pharmaceutically acceptable bases, such as non-toxic metal salts derived from metals of groups Ia, Ib, IIa and IIb, for example alkali metal salts, in particular sodium or potassium salts, alkaline earth metal salts, in particular calcium or magnesium salts, copper, aluminium or zinc salts, and also ammonium salts containing ammonia or organic amines or quaternary ammonium bases, such as aliphatic amines which can be C-hydroxylated, in particular mono-, di- or tri-lower alkylamines, for example methylamine, ethylamine or diethylamine, mono-, di- or tri-(hydroxy-lower alkyl)-amines, such as ethanolamine, diethanolamine or triethanolamine, tris-(hydroxymethyl)-methylamine or 2-hydroxy-tertiary butylamine, or N-(hydroxy-lower alkyl)-N,N-di-lower alkylamines or N-(polyhydroxy-lower alkyl)-N-lower alkylamines, such as 2-(dimethylamino)-ethanol or D-glucamine, or quarternary aliphatic ammonium hydroxides, for example tetrabutylammonium hydroxide. Both complete and partial salts, i.e. salts containing 1, 2, 3 or 4, preferably 2, equivalents of base per mole of acid of the formula I are embraced.

The compounds of the formula I and their salts have valuable pharmacological properties. In particular they have a pronounced regulating action on the calcium metabolism of warm-blooded animals. Thus in rats they effect a pronounced inhibition of bone resorption which can be demonstrated both in the test set-up specified in Acta Endocrinol. 78, 613–24 (1975) and by means of the PTH-induced increase in the serum calcium level after subcutaneous administration in doses of about 0.01 to about 1.0 mg/kg, and in the TPTX-(thyroparathyroidectomized) rate model by means of the experimental hypercalcaemia initiated by vitamin $D_3$ after the administration of doses of about 0.0005 to about 0.5 mg/kg subcutaneously and, in part, also perorally. The tumour hypercalcaemia induced by Walker-256 tumours is also inhibited after peroral administration of about 1.0 to about 100 mg/kg. They also exhibit, in doses of about 0.01 to about 1.0 mg/kg subcutaneously a marked inhibition of the progress of chronic arthritic processes in adjuvant arthritis of rats in the test-set up of Newbold, Brit. J. Pharmacology 21, 127 (1963) and of Kaibara et al., J. Exp. Med. 159, 1388–96 (1984). The indications of tumour-induced hypercalcaemia, bone metastases and Paget's disease are prominent in this respect.

The compounds of the formula I and salts thereof are therefore excellently suitable for use as active compounds for medicaments for the treatment of diseases which can be associated with disturbances of calcium metabolism, for example inflammatory processes in joints, degenerative processes in articular cartilage, osteoporosis, periodontitis, hyperparathyroidism and calcium deposits in blood vessels or in prosthetic implants.

The invention relates, for example, to compounds of the formula I in which $R_1$, n, X, $alk_1$ and $alk_2$ are as defined and $R_2$ is a monovalent aliphatic radical, and to salts thereof.

The invention relates primarily to compounds of the formula I in which $R_1$ is a phenyl, naphthyl, imidazolyl, thiazolyl, oxazolyl, pyridyl, pyrimidinyl or pyridazinyl radical which is unsubstituted or monosubstituted, disubstituted or trisubstituted, especially monosubstituted or disubstituted, by lower alkyl, lower alkoxy, lower alkylenedioxy, hydroxyl, halogen and/or trifluoromethyl, n is 0, 1, 2 or 3, X is oxy, thio, sulfinyl, sulfonyl, imino or lower alkylimino, $alk_1$ is lower alkylene, $R_2$ is hydrogen, lower alkyl or lower alkenyl and $alk_2$ is lower alkylene, and to salts thereof, in particular pharmaceutically acceptable salts thereof.

In particular, the invention relates in the first place to compounds of the formula I in which $R_1$ is a phenyl radical which is unsubstituted or monosubstituted or disubstituted by $C_1$–$C_4$alkyl, such as methyl, $C_1$–$C_4$alkoxy, such as methoxy, $C_1$–$C_4$alkylenedioxy, such as methylenedioxy or ethylenedioxy, hydroxyl, halogen having an atomic number up to and including 35, such as fluorine or chlorine and/or trifluoromethyl, n is 0 or, as a secondary choice, is 1 or 2, X is oxy, thio, sulfonyl, imino or $C_1$–$C_4$alkylimino, such as methylimino or ethylimino, $alk_1$ is $C_2$–$C_6$alkylene, such as ethylene, 1,3-propylene, 1,4-butylene, 1,5-pentylene or 1,6-hexylene, $R_2$ is hydrogen or $C_1$–$C_4$alkyl, such as methyl, ethyl, propyl or butyl, and $alk_2$ is $C_2$–$C_4$alkylene, such as ethylene, and to salts thereof, in particular pharmaceutically acceptable salts thereof.

In particular, the invention relates in the second place to compounds of the formula I in which $R_1$ is a pyridyl or pyrimidinyl radical which is unsubstituted or substituted by $C_1$–$C_4$alkyl, such as methyl, and/or phenyl which is unsubstituted or monosubstituted or disubstituted by $C_1$–$C_4$alkyl, such as methyl, $C_1$–$C_4$alkoxy, such as methoxy, $C_1$–$C_4$alkylenedioxy, such as methylenedioxy or ethylenedioxy, hydroxyl, halogen having an atomic number up to and including 35, such as fluorine or chlorine, and/or trifluoromethyl, n is 0, as a second choice, is 1 or 2, X is oxy, thio, imino or $C_1$–$C_4$alkylimino, such as methylimino or ethylimino, $alk_1$ is $C_2$–$C_6$alkylene, such as ethylene, 1,3-propylene, 1,4-butylene, 1,5-pentylene or 1,6-hexylene, $R_2$ is hydrogen or $C_1$–$C_4$alkyl, such as methyl, ethyl, propyl or butyl, and $alk_2$ is $C_2$–$C_4$alkylene, such as ethylene, and to salts thereof, in particular pharmaceutically acceptable salts thereof.

In particular, the invention relates, for example, to compounds of the formula I in which $R_1$ is a phenyl, naphthyl, pyridyl or pyrimidinyl radical which is unsubstituted or monosubstituted or disubstituted by $C_1$–$C_4$alkyl, such as methyl, $C_1$–$C_4$alkoxy, such as methoxy, $C_1$–$C_4$alkylenedioxy, such as methylenedioxy or ethylenedioxy, hydroxyl, halogen having an atomic number of up to and including 35, such as fluorine or chlorine, and/or trifluoromethyl, n is 0, 1 or 2, X is oxy, thio, sulfonyl, imino or $C_1$–$C_4$alkylimino, such as methylimino or ethylimino, $alk_1$ is $C_2$–$C_6$alkylene, such as ethylene, 1,3-propylene, 1,4-butylene, 1,5-pentylene or 1,6-hexylene, $R_2$ is $C_1$–$C_4$alkyl, such as methyl, ethyl, propyl or butyl, and $alk_2$ is $C_2$–$C_4$alkylene, such as ethylene, and to salts thereof, in particular pharmaceutically acceptable salts thereof.

The invention relates especially to compounds of the formula I in which $R_1$ is phenyl which is unsubstituted or substituted by $C_1$–$C_4$alkyl, such as methyl, $C_1$–$C_4$alkoxy, such as methoxy, hydroxyl, halogen having an atomic number of up to and including 35, such as fluorine or chlorine, or trifluoromethyl, or $R_1$ is unsubstituted pyridyl or pyrimidinyl, n is 0, X is oxy, thio, sulfonyl, imino or methylimino, $alk_1$ is $C_2$–$C_6$alkylene, such as ethylene, 1,3-propylene, 1,4-butylene, 1,5-pentylene or 1,6-hexylene, $R_2$ is hydrogen or $C_1$–$C_4$alkyl, such as methyl, ethyl, propyl or butyl, and $alk_2$ is ethylene, and to salts thereof, in particular to pharmaceutically acceptable salts thereof.

The invention relates especially, for example, to compounds of the formula I in which $R_1$ is phenyl which is unsubstituted or substituted by $C_1$–$C_4$alkyl, such as methyl, $C_1$–$C_4$alkoxy, such as methoxy, hydroxyl, halogen having an atomic number of up to and including 35, such as fluorine or chlorine or trifluoromethyl, or $R_1$ is unsubstituted pyridyl or pyrimidinyl, n is 0, X is oxy, thio, sulfonyl, imino or methylimino, $alk_1$ is $C_2$–$C_6$alkylene, such as ethylene, 1,3-propylene, 1,4-butylene, 1,5-pentylene or 1,6-hexylene, $R_2$ is $C_1$–$C_3$alkyl, such as methyl or ethyl, and $alk_2$ is ethylene, and to salts thereof, in particular to pharmaceutically acceptable salts thereof.

First and foremost, the invention relates in the first place to compounds of the formula I in which $R_1$ is phenyl which is unsubstituted or substituted by $C_1$–$C_4$alkyl, such as methyl, $C_1$–$C_4$alkoxy, such as methoxy, hydroxyl or halogen having an atomic number of up to and including 35, such as fluorine or chlorine, n is 0, X is oxy or thio, $alk_1$ is $C_2$–$C_4$alkylene, such as ethylene, 1,3-propylene or 1,4-butylene, $R_2$ is $C_1$–$C_3$alkyl, such as methyl, or, as a second choice, hydrogen and $alk_2$ is ethylene, and to salts thereof, in particular to pharmaceutically acceptable salts thereof.

First and foremost, the invention relates in the second place to compounds of the formula I in which $R_1$ is pyridyl or pyrimidyl which is unsubstituted or substituted by $C_1$–$C_4$alkyl, such as methyl, or by phenyl, n is 0, X is imino, oxy or thio which is unsubstituted or substituted by $C_1$–$C_4$alkyl, such as methyl or ethyl, $alk_1$ is $C_2$–$C_4$alkylene, such as ethylene, 1,3-propylene or 1,4-butylene, $R_2$ is $C_1$–$C_3$alkyl, such as methyl, or, as a second choice, hydrogen and $alk_2$ is ethylene, and to salts thereof, in particular to pharmaceutically acceptable salts thereof.

The invention relates especially to the compounds of the formula I mentioned in the examples and to salts thereof, in particular pharmaceutically acceptable salts thereof.

The invention also relates to a process based on methods known per se for the preparation of the compounds according to the invention. This process comprises (a) in a compound of the formula

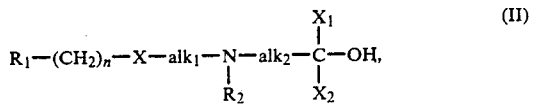

in which $R_1$, n, X, $alk_1$, $R_2$ and $alk_2$ are as defined above, $X_1$ is a functionally modified phosphono group and $X_2$ is a free or functionally modified phosphono group, converting functionally modified phosphono $X_1$ and, if appropriate, $X_2$ into the free phosphono group or (b) reacting with one another compounds of the formulae

and $$Y_2-alk_2-\underset{PO_3H_2}{\underset{|}{\overset{PO_3H_2}{\overset{|}{C}}}}-OH, \quad (IV)$$

in which one of the radicals $Y_1$ and $Y_2$ is a reactive esterified hydroxyl group Y and the other is a group of the formula $-N(R_2)-H$, or salts thereof, or reacting with one another under reducing conditions compounds of the formulae $$R_1-(CH_2)_n-X-alk'_1=O \quad (IIIa)$$

and $$H-\underset{R_2}{\underset{|}{N}}-alk_2-\underset{PO_3H_2}{\underset{|}{\overset{PO_3H_2}{\overset{|}{C}}}}-OH, \quad (IVa)$$

in which $alk_1'$ is a doubly bound radical corresponding to the radical $alk_1$, for example a correspondingly substituted lower alkanylylidene radical, or (c) reacting a compound of the formula $$R_1-(CH_2)_n-X-alk_1-\underset{R_2}{\underset{|}{N}}-alk_2-X_3, \quad (V)$$

in which $X_3$ is carboxyl, carbamyl or cyano, with a phosphorylating agent, hydrolysing the primary product and, in an intermediate of the formula $$R_1-(CH_2)_n-X-alk_1-\underset{R_2}{\underset{|}{N}}-alk_2-\underset{PO_3H_2}{\underset{|}{\overset{PO_3H_2}{\overset{|}{C}}}}-NH_2, \quad (VI)$$

or a salt thereof obtained using as starting materials compounds of the formula V in which $X_3$ is cyano or carbamyl, replacing the amino group by hydroxyl by treatment with nitrous acid or (d) reacting with one another compounds of the formulae $$R_1-(CH_2)_n-Y_3 \quad (VII)$$

and $$Y_4-alk_1-\underset{R_2}{\underset{|}{N}}-alk_2-\underset{PO_3H_2}{\underset{|}{\overset{PO_3H_2}{\overset{|}{C}}}}-OH, \quad (VIII)$$

in which $Y_3$ is a group of the formula $-X_0-H$ and $Y_4$ is reactive esterified hydroxyl Y or, if n is other than 0, $Y_3$ is a group Y and $Y_4$ is a group $-X_0-H$, $X_0$ being oxy, thio or imino X which is unsubstituted or has aliphatic substituents or is intermediately protected imino $-NR_0-$ in which $R_0$ is a customary amino protective group, and Y is reactive esterified hydroxyl, or salts thereof, or, in order to prepare compounds of the formula I in which X is an imino group which is unsubstituted or has aliphatic substituents, reacting with one another, under reducing conditions, compounds of the formulae $$R_1-(CH_2)_{\overline{n-1}}-CH=O \quad (VIIa)$$

and $$H-X_0'-alk_1-\underset{R_2}{\underset{|}{N}}-alk_2-\underset{PO_3H_2}{\underset{|}{\overset{PO_3H_2}{\overset{|}{C}}}}-OH, \quad (VIIIa)$$

or $$R_1-(CH_2)_{\overline{n}}X_0'-H \quad (VIIb)$$

and $$O=alk_1'-\underset{R_2}{\underset{|}{N}}-alk_2-\underset{PO_3H_2}{\underset{|}{\overset{PO_3H_2}{\overset{|}{C}}}}-OH, \quad (VIIIb)$$

in which $R_1$, n, $alk_1$, $R_2$ and $alk_2$ are as defined above and $X'_0$ is imino X which is unsubstituted or has aliphatic substituents or is intermediately protected imino $-NR_0-$ in which $R_0$ is a customary amino protective group, and in each case splitting off the amino protective group $R_0$, if present, and, if desired, splitting a resulting compound into another compound of the formula I, separating a mixture of isomers obtainable in accordance with the process into the components and isolating the particular preferred isomer and/or converting a free compound obtainable in accordance with the process into a salt or converting a salt obtainable in accordance with the process into the corresponding free compound.

The reactions according to the process and the preparation of novel starting materials or intermediates are effected analogously to the mode of reaction and formation of known starting materials and/or intermediates. The assistants customary in a particular case, such as catalysts, condensation agents and solvolysis agents and/or solvents or diluents and reaction conditions, such as temperature and pressure, and also, if appropriate, protective gases, are used in this regard, even if not mentioned expressly below.

Examples of suitable amino protective groups $R_0$ are α-aralkyl groups which are substituted or unsubstituted, such as benzyl or benzyloxy carbonyl groups, esterified or etherified hydroxymethyl groups, such as pivaloyloxymethyl, methoxymethyl, 2-chloroethoxymethyl or benzyloxymethyl, tetrahydropyranyl or tri-lower alkylsilyl, such as trimethylsilyl. The protective group is introduced, for example, by reacting the compound to be protected with an appropriate halogen derivative or with chloroiodomethane ($Cl-CH_2I$), an alkali metal pivalate, methanolate, 1,2-dichloroethanolate or benzyl alcoholate, for example sodium pivolate, methanolate, 1,2-dichloroethanolate or benzyl alcoholate, or with dihydropyran. Accordingly, protected imino is, for example, silylimino, such as trimethylsilylimino, but can also be phenyl-, diphenyl- or triphenyl-lower alkylimino, such as benzylimino, diphenylimino or triphenylimino.

Functionally modified phosphono groups to be converted into phosphono in accordance with process variant a) are present, for example, in an ester form, in particular a diester form of the formula $-P(=O)(OR_2)$ (IIa), in which OR is etherified hydroxyl, in particular lower alkoxy, lower alkanoyloxy-lower alkoxy or a phenoxy or α-phenyl-lower alkoxy group which is unsubstituted or substituted by lower alkyl, lower alkoxy, halogen, trifluoromethyl and/or hydroxyl, or is silyloxy, such as tri-lower alkylsilyloxy.

The conversion of functionally modified phosphono groups into free phosphono groups is effected kn a customary manner, such as by hydrolysis, for example in the presence of a mineral acid, such as hydrochloric or sulfuric acid, at about 80° C. to about 110° C., for example at the boil, or by reaction with a tri-lower alkyl halogenosilane, for example trimethylchlorosilane or especially trimethyliodosilane or trimethylbromosilane, preferably in methylene chloride within the temperature range from about 0° C. to about 40° C., followed by treatment with water. α-Phenyl-lower alkyl esters can also be converted into compounds of the formula I by hydrogenolysis, for example reaction with hydrogen in the presence of a hydrogenation catalyst, such as a nickel or noble metal catalyst, for example palladium-on-charcoal, preferably in a lower alkanol and under normal conditions of temperature and pressure.

The starting materials of the formula II can, for example, be prepared by subjecting a compound of the formula

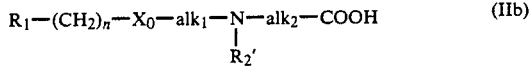

in which $X_0$ is oxy, thio or imino X which is unsubstituted or has aliphatic substituents or is intermediately protected imino $-NR_0-$ in which $R_0$ is a customary amino protective group, and $R_2'$ is a group $R_2$ or an amino protective group $R_0$, or preferably the anhydride or acid chloride thereof, to a condensation reaction with a corresponding phosphorous acid triester of the formula $P(OR)_3$ (IIc), at, for example, 0° C. to about 60° C., to give a compound of the formula

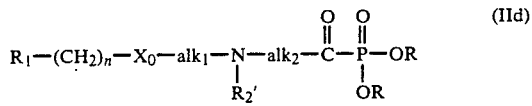

and reacting the latter further with a phosphorous acid diester of the formula $H-P(=O)(OR)_2$ (IIe) or $P(OH)(OR)_2$ (IIf) in the presence of a di-lower alkylamine, for example diethylamine, or an alkali metal lower alkanolate, for example sodium methanolate, to give the corresponding compound of the formula

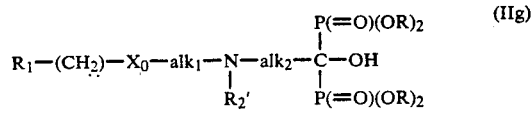

if appropriate splitting off the amino protective group(s) $R_0$ and/or, if desired, introducing a radical $R_2$ which is other than hydrogen, for example as described below under (b).

Insofar as they are not known, starting materials of the formula IIb can, for example, be prepared by reacting a corresponding compound of the formula $R_1-(CH_2)_n-X_0-alk_1-N(R_2')-H$ (IIh) in which $R_2'$ is a group $R_2$ or an amino protective group $R_0$ with a compound of the formula $Y-alk_2-COOH$ (IIi) in which Y is halogen, such as bromine, or, for the preparation of compounds of the formula IIb in which $alk_2$ is 1,2-lower alkylene, for example ethylene, with a compound of the formula $alk_0-COOR$ (IIj) in which $alk_0$ is lower alk-1-enyl, in each case hydrolysing the ester obtained to give the acid, converting the latter into an anhydride or chlorinating it, for example by means of phosphorus pentachloride, splitting off an amino protective group which may be present and, if necessary or desired, introducing aliphatic substituents into the amino group which has been set free.

Reactive esters III or IV to be used in accordance with process variant (b) contain, as reactive esterified hydroxyl groups, for example, a halogen atom, such as chlorine, bromine or iodine, or a sulfonyloxy group, for example methanesulfonyloxy or p-toluenesulfonyloxy.

The reaction with the reactive esters mentioned is effected, for example, in the presence of a base, such as an alkali metal hydroxide or alkaline earth metal hydroxide, for example sodium hydroxide, or a quaternary ammonium hydroxide, for example tetrabutylammonium hydroxide, advantageously in the presence of a solvent or diluent, for example a lower alkanol, di-lower alkyl ketone or cycloaliphatic ether, for example isopropanol, methyl ethyl ketone, dioxane or tetrahydrofuran.

The reaction with oxo compounds IIIa is carried out, for example, in the presence of an alkali metal borohydride, for example sodium cyanoborohydride, or, in particular, by treatment with formic acid.

The starting materials of the formula IV can, for example, be prepared by reacting a compound of the formula $Y_2-alk_2-X_3$ (IVb) in a customary manner, for example in chlorobenzene, with phosphorous acid and phosphorus trichloride or with phosphoric acid and an excess of phosphorus tribromide and subsequently working up the product by hydrolysis. Starting materials IVa can be prepared in an analogous manner by reacting compounds of the formula $R_0-N(R_2)-alk_2-X_3$ (IVc) with phosphorous acid and phosphorus trichloride, $R_0$ being a customary amino protective group.

Examples of phosphorylating agents suitable for process variant (c) are phosphorus trioxide, phosphorus trihalides mixed with phosphorous acid or phosphoric acid, phosphorus oxichloride or phosphorus pentachloride or phosphorus trichloride mixed with chlorine. Phosphorus trioxide is preferred, and is preferably formed in situ by reacting phosphorus trichloride with phosphorous acid or the phosphorous acid component, preferably by reacting with an excess of phosphorus trichloride containing aqueous phosphoric acid, for example with commercially available phosphoric acid of about 75% to 95%, preferably about 85%, strength. It is advantageous to carry out the reaction by heating, for example at about 70° to 120° C., in a suitable solvent, such as tetrachloroethane, trichloroethane, chlorobenzene, chlorotoluene or paraffin oil, and to work up the product by hydrolysis.

The treatment of intermediates of the formula VI with nitrous acid is effected in a customary manner by liberating the latter in aqueous solution from one of its salts, for example from sodium nitrite, by treatment with an acid, for example by the action of hydrochloric acid, a corresponding unstable diazonium salt, for example diazonium chloride, being formed as an intermediate and splitting off nitrogen with the introduction of the α-hydroxyl group.

Insofar as they are not known, the starting materials of the formula V can, for example, be prepared by reacting a corresponding compound of the formula $R_1O(CH_2)_n$-$X_0$-$alk_1$-$N(R_2')$-H (IIh) with a compound of the formula Y-$alk_2$-$X_3$ (Va) in which Y is halogen, such as bromine, or, for the preparation of compounds of the formula V in which $alk_2$ is 1,2-lower alkylene, for example ethylene, with a compound of the formula $alk_0$-$X_3$ (Vb) in which $alk_0$ is a lower alk-1-enyl radical, splitting off in each case the amino protective group, if present, and, if desired, in each case hydrolysing the primary product obtained to give the acid.

Reactive esters VII or VIII to be used in accordance with process variant (d) contain, as reactive esterified hydroxyl groups, for example, a halogen atom, such as chlorine, bromine or iodine, or a sulfonyloxy group, for example methanesulfonyloxy or p-toluenesulfonyloxy.

The reaction with the reactive esters mentioned is effected, for example, in the presence of a base, such as an alkali metal hydroxide or alkaline earth metal hydroxide, for example sodium hydroxide, or a quaternary ammonium hydroxide, for example tetrabutylammonium hydroxide, with advantage in the presence of a solvent or diluent, for example a lower alkanol, di-lower alkyl ketone or cycloaliphatic ether, for example isopropanol, methyl ethyl ketone, dioxane or tetrahydrofuran.

Using thiols VII or VIII or phenols or thiophenols VII as starting materials, suitable basic condensation agents are also, or preferably, alkali metal carbonates, such as sodium carbonate or potassium carbonate, advantageously in an aliphatic or cycloaliphatic ketone, for example in acetone or cyclohexanone, the reaction being preferably carried out at an elevated temperature for example within the temperature range from about 50° to about 100° C., for example at the boil.

The reaction with oxo compounds VIIa or VIIIb is carried out, for example, in the presence of an alkali metal borohydride, for example sodium cyanoborohydride, or, in particular, by treatment with formic acid. In particular, a compound of the formula IVa in which $R_D$ is a radical $R_1$-$(CH_2)$-$alk_1$- can be substituted by a lower alkyl radical $R_2$ under reducing conditions by means of a lower alkanal, for example formaldehyde, and formic acid, or, as a second choice, by means of a reactive ester of a lower alkanol or lower alkenol in a customary manner, preferably in the presence of a basic condensation agent, such as an alkali metal lower alkanolate.

The starting materials of the formula VII, VIIa and VIIb are for the most part known. Starting materials of the formulae VIII, VIIIa and VIIIb can, for example, be prepared by reacting a compound of the formula Y-$alk_2$-$X_3$ (VIIId) in a customary manner, for example in chlorobenzene, with phosphorous acid and phosphorus trichloride or with phosphoric acid and an excess of phosphorus tribromide, subsequently working up the product by hydrolysis and reacting the resulting compound of the formula

(VIIIe)

further in a customary manner with a compound of the formulae $Y_4$-$alk_1$-$N(R_2')$-H (VIIIf), H-$X_0$-$alk_1$-$N(R_2')$-H (VIIIg) or O=$alk_1'$-$N(R_2')$-H (VIIIh).

The liberation of radicals which are intermediately protected, for example by splitting off an amino protective group $R_0$, is effected in a customary manner, for example by hydrogenolysis, for example in the presence of platinum or palladium catalysts, or by solvolysis, such as mild hydrolysis, for example by treatment with water under neutral or weakly acid conditions, for example by the action of dilute aqueous mineral acids or carboxylic acids, for example dilute hydrochloric acid or acetic acid.

Compounds obtainable in accordance with the process can be converted in a customary manner into other compounds of the formula I.

Thus a monovalent aliphatic radical $R_2$ can be introduced into compounds of the formula I in which $R_2$ is hydrogen in a customary manner by reaction with a reactive ester of the formula $R_2$-Y (IX) in which Y is reactive esterified hydroxyl, for example a halogen atom, such as chlorine, bromine or iodine, or a sulfonyloxy group, for example methanesulfonyloxy or p-toluenesulfonyloxy, or by reaction with an aliphatic aldehyde or ketone of the formula $R_2$=O (IXa) under reducing conditions. In particular, in order to prepare compounds of the formula I in which $R_2$ is a monovalent aliphatic radical and salts thereof, it is possible (e) to react with one another compounds of the formulae

(IX)

and

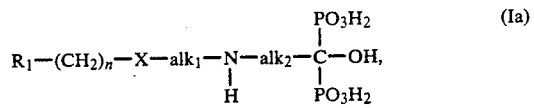
(Ia)

in which $R_1$, n, X, $alk_1$, $R_2$ and $alk_2$ have the meanings indicated and Y is reactive esterified hydroxyl, or salts thereof, or to react under reducing conditions, compounds of the formulae

(IXa)

and

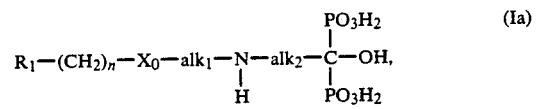
(Ia)

in which $R_1$, n, X, $alk_1$ and $alk_2$ are as defined above, $X_0$ is oxy, thio or imino X which is unsubstituted or has aliphatic substituents or is intermediately protected imino —$NR_0$— in which $R_0$ is a customary amino protective group, and $R_2''$ is a corresponding radical which is doubly bound to the radical $R_2$, for example lower alkylidene.

The reaction with the reactive esters mentioned (IX) is effected, for example, in the presence of a base, such as an alkali metal hydroxide or alkaline earth metal hydroxide, for example sodium hydroxide, or a quaternary ammonium hydroxide, for example tetrabutylammonium hydroxide, advantageously in the presence of a solvent or diluent, for example a lower alkanol, di-lower alkyl ketone or cycloaliphatic ether, for example isopropanol, methyl ethyl ketone, dioxane or tetrahydrofuran. The reaction with oxo compounds (IXa) is carried out, for example, in the presence of an alkali metal borohydride, for example sodium cyanoborohydride, or, in particular, by treatment with formic acid. In a preferred embodiment a corresponding compound of the formula Ia can be substituted by a lower alkyl radical $R_2$ under reducing conditions by means of a lower alkanal, for example formaldehyde, and formic acid.

It is also possible to oxidize compounds of the formula I in which X is thio in a customary manner to give the corresponding compound of the formula I in which X is sulfinyl or sulfonyl, for example by treatment with an inorganic peroxy compound, for example hydrogen peroxide, persulfuric acid, or an organic peroxy compound, such as perbenzoic acid or m-chloroperbenzoic acid.

It is also possible to introduce substituents into the radical $R_1$ of compounds of the formula I, for example lower alkyl by reaction with a lower alkyl halide in the presence of aluminium trichloride, lower alkoxy, for example by nitration, reduction of the nitro group to give the amino group, diazotization of the latter and treatment of the diazonium salt formed with the corresponding lower alkanol under hot conditions, and halogen, for example, by treatment with chlorine or bromine, advantageously in the presence of a Lewis acid, for example iron-III chloride. It is also possible, however, to replace halogen by trifluoromethyl, for example by treatment with trifluoroiodomethane in the presence of copper powder or copper-I iodide.

Compounds of the formula I in which X is imino can also be substituted by an aliphatic radical, for example as described above for the introduction of a radical $R_2$ which is other than hydrogen.

Depending on the choice of starting materials and procedures, the novel compounds can be present in the form of one of the possible isomers, for example, depending on the number of asymmetric carbon atoms, as optical isomers, such as in the form of an enantiomer, such as antipodes or diastereomers or mixtures thereof, such as mixtures of enantiomers, for example racemates, mixtures of diastereomers or mixtures of racemates.

Resulting mixtures of diastereomers and mixtures of racemates can be separated into the pure diastereomers or racemates, respectively, in a known manner on the basis of the physicochemical differences between the constituents, for example by chromatography and/or fractional crystallization. Resulting racemates can also be resolved into the optical antipodes by known methods, for example by recrystallization from an optically active solvent, with the help of microorganisms by reacting a compound of the formula I with an optically active base or with an optically active alcohol and separating the resulting diastereomeric esters, for example on the basis of their different solubilities, into the diastereomers, from which the enantiomers can be liberated by the action of suitable agents. Racemates of the formula I can also be resolved, by reaction with an optically active base, into mixtures of the diastereomeric salts and separation of the latter into the diastereomers, from which the enantiomers can be liberated in the manner customary in each case.

Examples of optically active bases which are customary for this purpose are optically active alkaloids, such as quinine, cinchonine, brucine and the like, or, in particular, α-phenylethylamine.

It is also possible to convert resulting salt-forming compounds into salts in a manner known per se, for example by reacting a solution of the free solvent in a suitable solvent or solvent mixture with an appropriate base or with a suitable ion exchanger.

Resulting salts can be converted into the free compounds in a manner known per se, for example by treatment with an acid, such as a mineral acid, for example hydrochloric acid.

Resulting salts can be converted into other salts in a manner known per se, for example by treatment with a suitable base, such as sodium hydroxide or potassium hydroxide, ammonia or a suitable amine.

The compounds of the formula I, including their salts, can also be obtained in the form of hydrates or can occlude the solvent used for crystallization.

Because of the close relationship between the novel compounds in the free form and in the form of their salts, what is stated in the preceding and following text in respect of the free compounds or the salts thereof also applies by analogy to the corresponding salts and free compounds, respectively.

The invention also relates to those embodiments of the process in which a compound obtainable as an intermediate at any stage of the process is used as the starting material and the remaining stages are carried out, or a starting material is used in the form of a salt, or, in particular, is formed under the conditions of the reaction.

The novel starting materials, which have been specially developed for the preparation of the compounds according to the invention, in particular the choice of starting materials leading to the compounds of the formula I which have been characterized initially as preferred, the processes for their preparation and their use as intermediates also form an object of the invention.

The novel compounds of the formula I can, for example, be used in the form of pharmaceutical formulations containing a therapeutically effective amount of the active substance, if appropriate together with inorganic or organic, solid or liquid, pharmaceutically acceptable excipients which are suitable for enteral administration, for example oral or parenteral administration. Thus tablets or gelatin capsules containing the active ingredient together with diluents, for example lactose, dextrose, sucrose, mannitol, sorbitol or cellulose, and/or lubricants, for example silica, talc, stearic acid or salts thereof, such as magnesium stearate or calcium stearate, and/or polyethylene glycol. Tablets can also contain binders, for example magnesium aluminium silicate, starches, such as maize, wheat, rice or arrow root starch, gelatin, tragacanth, methyl cellulose, sodium carboxymethyl cellulose and/or polyvinylpyrrolidone, and, if desired, disintegrants, for example starches, agar, alginic acid or a salt thereof, for example sodium alginate, and/or effervescent mixtures, or absorbents, dyes, flavouring substances and sweeteners. The novel compounds of the formula I can also be used in the form of formulations capable of being administered parenterally or in the form of infusion solutions. Such solutions are preferably isotonic aqueous solutions or suspensions, it being possible to prepare the latter before use, for example in the case of lyophilized formulations containing the active ingredient on its own or together with an excipient, for example mannitol. The pharmaceutical formulations can be sterilized and/or contain adjuncts, for example preservatives, stabilizers, wetting agents and/or emulsifiers, solubilizers, salts for regulating the osmotic pressure and/or buffers. The present pharmaceutical formulations, which, if desired can contain further pharmacologically active substances, are prepared in a manner known per se, for example by means of conventional mixing, granulating, coating, solution or lyophilizing processes, and contain from about 0.1% to 100%, in particular from about 1% to about 50% of the active ingredient, up to about 100% in the case of lyophilizates.

Products suitable for parenteral administration are primarily aqueous solutions of the active ingredient in a water-soluble form, for example in the form of a water-soluble, pharmaceutically acceptable salt, and also suspensions of the active ingredient, such as oily injection suspensions, in which case suitable lipophilic solvents or vehicles, such as fatty oils, for example sesame oil, or synthetic fatty esters, for example ethyl oleate, and also triglycerides are used, or aqueous injection suspensions containing substances which increase the viscosity, for example sodium carboxymethyl cellulose, sorbitol and/or dextran, and, if appropriate stabilizers.

The invention also relates to the use of compounds of the formula I for the treatment of diseases due to disturbances of calcium metabolism, preferably by the provision of pharmaceutical formulations. The dosage of the compound of the formula I according to the invention can depend on various factors such as the mode of application, species, age and/or individual condition. Single doses contain, for example, from about 0.01 to about 0.1 mg, preferably 0.02 to 0.08 mg, per kilogram of body weight in the case of parenteral administration and about 0.2 to about 2.5 mg, preferably 0.3 to 1.5 mg, per kilogram of body weight in the case of oral administration. The preferred single doses thus amount to about 0.5 to 5.0 mg in the case of parenteral administration and to about 10 to 100 mg in the case of oral administration. The doses to be administered daily in the case of oral administration are between about 0.25 and about 10 mg/kg and for warm-blooded animals having a body weight of about 70 kg, preferably between about 20 mg and about 500 mg.

The following examples serve to illustrate the invention; temperatures are quoted in degrees Centigrade and pressures in mbar.

EXAMPLE 1

27.3 g (0.1 mol) of 3-[N-(3-phenoxypropyl)-N-methylamino]-propionic acid hydrochloride, together with 13.4 ml of 85% phosphoric acid and 50 ml of chlorobenzene, are heated at 100° with stirring and under reflux. 27 ml of phosphorus trichloride are then added dropwise at 100°, in the course of which evolution of gas takes place. In the course of 30 minutes the reaction mixture deposits a thick mass. It is heated for a further 2 hours 100° and the supernatant chlorobenzene is then decanted off. The tough mass which remains, together with 100 ml of 4-N hydrochloric acid, is heated at the boil for 3 hours, with stirring and under reflux. The mixture is filtered while hot with the addition of charcoal, and the filtrate is diluted with acetone, when 3-[N-(3-phenoxypropyl)-N-methylamino]-1-hydroxypropane-1,1-diphosphonic acid is precipitated in the form of crystals; melting point 198°-200° (decomp.).

The starting material can be prepared, for example, in the following way:

23.75 g (0.15 mol) of N-(3-phenoxypropyl)-N-methylamine are initially taken in 50 ml of diethyl ether, and 15.1 ml of ethyl acrylate are added slowly, with stirring. A clear solution is formed with a slight increase in the temperature. The mixture is left to stand overnight at room temperature and the diethyl ether is then removed by distillation. The oil which remains is crude ethyl 3-[N-(3-phenoxypropyl)-N-methylamino]-propionate.

The ester obtained is heated to reflux temperature for 24 hours in 600 ml of 4N hydrochloric acid. The mixture is then evaporated completely under reduced pressure, and the crystalline residue is triturated with acetone. Washing, filtering off with suction and drying the crystals gives 3-[N-(3-phenoxypropyl)-N-methylamino]-propionic acid hydrochloride, melting point 127°-128°.

EXAMPLE 2

3-{N-[2-(4-Methoxyphenoxy)-ethyl]-amino}-1-hydroxypropane-1,1-disphosphonic acid, melting point 118°-124°, is obtained in a manner analogous to that described in Example 1, starting from 3-{N-[2-(4-Methoxyphenoxy)-ethyl]-amino}-propionic acid hydrochloride, melting point 105°-108°.

EXAMPLE 3

3-[N-(2-phenoxyethyl)-N-methylamino]-1-hydroxypropane-1,1-diphosphonic acid, melting point 125°-130° (decomp.), is obtained in a manner analogous to that described in Example 1, starting from 3-[N-(2-phenoxyethyl)-N-methylamino]-propionic acid hydrochloride, melting point 104°-106°.

EXAMPLE 4

3-[N-(3-phenoxypropyl)-N-ethylamino]-1-hydroxypropane-1,1-diphosphonic acid, melting point 195°-197° (decomp.), is obtained in a manner analogous to that described in Example 1, starting from 3-[N-(3-phenoxypropyl)-N-ethylamino]-propionic acid hydrochloride, melting point 105°-108°.

EXAMPLE 5

3-[N-(3-Phenoxypropyl)-N-propylamino]-1-hydroxypropane-1,1-diphosphonic acid, melting point 197°-199° (decomp.), is obtained in a manner analogous to that described Example 1, starting from 3-[N-(3-phenoxypropyl)-N-propylamino]-propionic acid hydrochloride (oil).

EXAMPLE 6

3-[N-(3-Phenoxypropyl)-N-butylamino]-1-hydroxypropane-1,1-diphosphonic acid, melting point 181°-183° (decomp.), is obtained in a manner analogous to that described in Example 1, starting from 3-[N-(3-phenoxypropyl)-N-butylamino]-propionic acid hydrochloride (oil).

EXAMPLE 7

3-{N-[3-(4-Methoxyphenoxy)-propyl]-N-methylamino}-1-hydroxypropane-1,1-diphosphonic acid, melting point 128°-130° (decomp.), is obtained in a manner analogous to that described in Example 1, starting from 3-{N-[3-(4-methoxyphenoxy)-propyl]-N-methylamino}-propionic acid hydrochloride, melting point 115°-116°.

EXAMPLE 8

3-{N-[2-(2-Hydroxyphenoxy)-ethyl]-N-methylamino}-1-hydroxypropane-1,1-diphosphonic acid, melting point 141°-145° (decomp.) is obtained in a manner analogous to that described in Example 1 starting from 3-{N-[2-(2-methoxyphenoxy)-ethyl]-N-methylamino}-propionic acid hydrochloride, melting point 147°-149°, with simultaneous ether cleavage at the methoxy group.

EXAMPLE 9

3-{N-[3-(4-Chlorophenoxy)-propyl]-N-methylamino}-1-hydroxypropane-1,1-diphosphonic acid, melting point 155°-162° (decomp.), is obtained in a manner analogous to that described in Example 1, starting from 3-{N-[3-(4-chlorophenoxy)-propyl]-N-methylamino}-propionic acid hydrochloride, melting point 129°-132°.

EXAMPLE 10

3-{{N-{3-[N'-(Pyrid-2-yl)-N'-methylamino]-propyl}-N-methylamino}}-1-hydroxypropane-1,1-disphosphonic acid is obtained in a manner analogous to that described in Example I, starting from 3-{{N-{3-[N'-(Pyrid-2-yl)-N'-methylamino]-propyl}-N-methylamino}} propionic acid hydrochloride (resin). The compound obtained is present in the form of the phosphoric acid addition salt of empirical formula $C_{13}H_{25}N_3O_7P_2 \times \frac{3}{4}H_3PO_4 \times H_2O$, melting point 158°-161° (decomp.).

EXAMPLE 11

3-[N-(2-Phenylthioethyl)-N-methylamino]-1-hydroxypropane-1,1-disphonic acid, melting point 165°-168° (decomp.), is obtained in a manner analogous to that described in Example 1, starting from 3-[N-(2-phenylthioethyl)-N-methylamino]propionic acid hydrochloride, melting point 103°-104°.

EXAMPLE 12

3-[N-(3-Phenoxypropyl)amino]-1-hydroxypropane-1,1-diphosphonic acid, melting point 148°-155° (decomp.), is obtained in a manner analogous to that described in Example 1, starting from 3-[N-(3-phenoxypropyl)-amino]-propionic acid hydrochloride, melting point 121°-122°.

EXAMPLE 13

3-{N-[2-(4-Chlorophenoxy)-ethyl]-N-methylamino]-1-hydroxypropane-1,1-diphosphonic acid, melting point 216°-218° (decomp.), is obtained in a manner analogous to that described in Example 1, starting from 3-{N-[2-(4-chlorophenoxy)-ethyl]-N-methylamino}-propionic acid hydrochloride, melting point 176°-179°.

EXAMPLE 14

3-{N-[3-(4-Fluorophenoxy)-propyl]-N-methylamino]-1-hydroxypropane-1,1-diphosphonic acid, melting point 165°-172° (decomp.), is obtained in a manner analogous to that described in Example 1, starting from 3-{N-[3-(4-fluorophenoxy)-propyl]-N-methylamino}-propionic acid hydrochloride, melting point 119°-121°.

EXAMPLE 15

3-[N-(4-Phenoxybutyl)-N-methylamino]-1-hydroxypropane-1,1-diphosphonic acid, melting point 153°-156° (decomp.), is obtained in a manner analogous to that described in Example 1, starting from 3-[N-(4-phenoxybutyl)-N-methylamino]-propionic acid hydrochloride, melting point 114°-116°.

EXAMPLE 16

3-[N-(6-Phenoxyhexyl)-N-methylamino]-1-hydroxypropane-1,1-diphosphonic acid, melting point 183°-187° (decomp.), is obtained in a manner analogous to that described in Example 1, starting from 3-[N-(6-phenoxyhexyl)-N-methylamino]-propionic acid hydrochloride, melting point 108°-109°.

EXAMPLE 17

The following compounds can be prepared in a manner analogous to that described in Example 1:
3-[N-(3-phenylthiopropyl)-N-methylamino]-1-hydroxypropane-1,1-diphosphonic acid;
3-{N-[3-(3-methylphenoxy)propyl]-N-methylamino}-1-hydroxypropane-1,1-diphosphonic acid;
3-[N-(3-(4-methoxyphenoxy)-propylamino]-1-hydroxypropane-1,1-diphosphonic acid;
3-[N-(4-(phenylthiobutyl)-N-methylamino]-1-hydroxypropane-1,1-disphosphonic acid;
3-{N-[2-(3-trifluoromethylphenylamino)ethyl]-N-methylamino}-1-hydroxypropane-1,1-diphosphonic acid;
3-{N-[3-(2-pyridylamino)-propyl]-N-methylamino}-1-hydroxypropane-1,1-diphosphonic acid;
3-{N-[3-(2-pyrimidinylamino)propyl]-N-methylamino}-1-hydroxypropane-1,1-diphosphonic acid and
3-[N-(3-(benzosulfonyl)-ethyl]-N-methylamino]-1-hydroxypropane-1,1-diphosphonic acid.

EXAMPLE 18

3-{N-[3-(3-Methylphenoxy)-propyl]-N-methylamino}-1-hydroxypropane-1,1-diphosphonic acid, melting point 152°-158° (decomp.), is obtained in a manner analogous to that described in Example 1, starting from 3-{N-[3-(3-methylphenoxy)-propyl]-N-methylamino]-propionic acid hydrochloride, melting point 109°-114°.

EXAMPLE 19

3-{{N-{3-[N'-(Pyrid-2-yl)-N'-ethylamino]-propyl}-N-ethylamino}}-1-hydroxypropane-1,1-diphosphonic acid can be prepared in a manner analogous to that described in Example 1.

EXAMPLE 20

0.92 g of 3-[N-(3-phenoxypropyl)amino]-1-hydroxypropane-1,1-diphosphonic acid, together with 75 ml of 98% formic acid and 0.5 ml of 35% aqueous formaldehyde solution, are heated to reflux temperature with stirring for 20 hours. The reaction mixture is concentrated under reduced pressure, and the residue is crystallized from acetone. This gives 3-[N-(3-phenoxypropyl)-N-methylamino]-1-hydroxypropane-1,1-diphosphonic acid, melting point 198°-200° (decomp.).

EXAMPLE 21

Tablets each containing 50 mg of 3-[N-(3-phenoxypropyl)-N-methylamino]-1-hydroxypropane-1,1-diphosphonic acid or a salt thereof, for example the disodium salt, can be prepared as follows:

| Composition (10,000 tablets) | |
| --- | --- |
| Active ingredient | 500.0 g |

-continued

| Composition (10,000 tablets) | |
|---|---|
| Lactose | 500.0 g |
| Potato starch | 325.0 g |
| Gelatin | 8.0 g |
| Talc | 60.0 g |
| Magnesium stearate | 10.0 g |
| Silicon dioxide (finely divided) | 20.0 g |
| Ethanol | q.s. |

The active ingredient is mixed with the lactose and 292 g of potato starch, and the mixture is moistened with an ethanolic solution of the gelatin and granulated through a sieve. After the granules have dried, the remainder of the potato starch, the magnesium stearate and the silicon dioxide are admixed and the mixture compressed to give tablets each weighing 145.0 mg and containing 50.0 mg of active ingredient, which can, if desired, be provided with breaking grooves to enable the dosage to be more finely adjusted.

EXAMPLE 22

Lacquered tablets each containing 100 mg of 3-[N-(3-phenoxypropyl)-N-methylamino]-1-hydroxypropane-1,1-diphosphonic acid or a salt thereof, for example the disodium salt, can be prepared as follows:

| Composition (for 1,000 lacquered tablets) | |
|---|---|
| Active ingredient | 100.0 g |
| Lactose | 100.0 g |
| Maize starch | 70.0 g |
| Talc | 8.5 g |
| Calcium stearate | 1.5 g |
| Hydroxypropylose | 2.36 g |
| Shellac | 0.64 g |
| Water | q.s. |
| Methylene chloride | q.s. |

The active ingredient, the lactose and 40 g of the maize starch are mixed, moistened with a paste prepared (by heating) from 15 g of maize starch and water and granulated. The granules are dried and the remainder of the maize starch, the talc and the calcium stearate are added and mixed with the granules. The mixture is compressed to give tablets (weight: 280 mg), and these tablets are lacquered with a solution of the hydroxypropylmethyl cellulose and the shellac in methylene chloride; final weight of the lacquered tablet: 283 mg.

EXAMPLE 23

Hard gelatin capsules each containing 100 mg of active ingredient, for example 3-[N-(3-phenoxypropyl)-N-methylamino]-1-hydroxypropane-1,1-diphosphonic acid or a salt thereof, for example the disodium salt, can, for example, be prepared in the following way:

| Composition (for 1,000 capsules) | |
|---|---|
| Active ingredient | 100.0 g |
| Microcrystalline cellulose | 30.0 g |
| Sodium laurylsulfate | 2.0 g |
| Magnesium stearate | 8.0 g |

Using a sieve of mesh width 0.2 mm, the sodium laurylsulfate is sieved onto the lyophilised active ingredient. The two components are intimately mixed. The microcrystalline cellulose is then sieved onto the mixture through a sieve of mesh width 0.9 mm. The mixture is again intimately mixed for 10 minutes. Finally, the magnesium stearate is sieved on using a sieve of mesh width 0.8 mm. After being mixed for a further 3 minutes, 390 mg of the resulting formulation are filled into each hard gelatin capsule of size 0.

EXAMPLE 24

A 0.2% injection or infusion solution of 3-[N-(3-phenoxypropyl)-N-methylamino]-1-hydroxypropane-1,1-diphosphonic acid or one of its salts, for example its disodium salt, can, for example, be prepared in the following way:

| Composition (for 1,000 ampoules) | |
|---|---|
| Active ingredient | 5.0 g |
| Sodium chloride | 22.5 g |
| Phosphate buffer pH 7.4 | 300.0 g |
| Deionized water | ad 2500.0 ml |

The active ingredient is dissolved in 1000 ml of water and the solution is filtered through a microfilter. The buffer solution is added and the mixture is made up to 2500 ml with water. Dosage unit forms are prepared by filling 1.0 to 2.5 ml in each case into glass or plastic ampoules, which then contain 2.0 or 5.0 mg, respectively, of active ingredient in each case.

EXAMPLE 25

Pharmaceutical formulations containing another compound of the formula I according to one of Examples 2 to 20 can also be prepared in a manner analogous to that in Examples 21 to 24.

What is claimed is:

1. A compound of the formula I

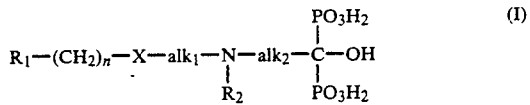

wherein $R_1$ is a phenyl, naphthyl, imidazolyl, thiazolyl, oxazolyl, pyridyl, pyrimidinyl or pyridazinyl radical which is unsubstituted or monosubstituted, disubstituted or trisubstituted by lower alkyl, lower alkoxy, lower alkylenedioxy, hydroxyl, halogen and/or trifluoromethyl, n is 0, 1, 2 or 3, X is oxy, thio, sulfinyl, sulfonyl, imino or lower alkylimino, $alk_1$ is lower alkylene, $R_2$ is hydrogen, lower alkyl or lower alkenyl and $alk_2$ is lower alkylene or a pharmaceutically acceptable salt thereof.

2. A compound according to claim 1 of the formula I in which $R_1$ is a phenyl radical which is unsubstituted or monosubstituted or disubstituted by $C_1$-$C_4$alkyl, $C_1$-$C_4$alkoxy, $C_1$-$C_4$alkylenedioxy, hydroxyl, halogen having an atomic number up to and including 35 and/or trifluoromethyl, n is 0, 1 or 2, X is oxy, thio, sulfonyl, imino or $C_1$-$C_4$alkylimino, $alk_1$ is $C_2$-$C_6$alkylene, $R_2$ is hydrogen or $C_1$-$C_4$alkyl and $alk_2$ is $C_2$-$C_4$alkylene, or a pharmaceutically acceptable salt thereof.

3. A compound according to claim 1 of the formula I in which $R_1$ is a pyridyl or pyrimidinyl radical which is unsubstituted or substituted by $C_1$-$C_4$alkyl and/or phenyl which is unsubstituted or monosubstituted or disubstituted by $C_1$-$C_4$alkyl, $C_1$-$C_4$alkoxy, $C_1$-$C_4$alkylenedioxy, hydroxyl, halogen having an atomic number up to and including 35 and/or trifluoromethyl, n is 0, 1 or 2, X is oxy, thio, imino or $C_1$-$C_4$alkylimino, $alk_1$ is $C_2$-$C_6$alkylene, $R_2$ is hydrogen or $C_1$-$C_4$alkyl and $alk_2$ is $C_2$–$C_4$alkylene, or a pharmaceutically acceptable salt thereof.

4. A compound according to claim 1 of the formula I in which $R_1$ is phenyl which is unsubstituted or substituted by $C_1$–$C_4$alkyl, $C_1$–$C_4$alkoxy, hydroxyl, halogen having an atomic number up to and including 35 or trifluoromethyl, or $R_1$ is unsubstituted pyridyl or pyrimidinyl, n is 0, X is oxy, thio, sulfonyl, imino or methylimino, $alk_1$ is $C_2$–$C_6$alkylene, $R_2$ is hydrogen or $C_1$–$C_4$alkyl and $alk_2$ is ethylene, or a pharmaceutically acceptable salt thereof.

5. A compound according to claim 1 of the formula I in which $R_1$ is phenyl which is unsubstituted or substituted by $C_1$–$C_4$alkyl, $C_1$–$C_4$alkoxy or halogen having an atomic number up to and including 35, n is 0, X is oxy or thio, $alk_1$ is $C_2$–$C_4$alkylene, $R_2$ is $C_1$–$C_3$alkyl or hydrogen and $alk_2$ is ethylene, or a pharmaceutically acceptable salt thereof.

6. A compound according to claim 1 of the formula I in which $R_1$ is pyridyl or pyrimidinyl which is unsubstituted or substituted by $C_1$–$C_4$alkyl or phenyl, n is 0, X is imino which is unsubstituted or substituted by $C_1$–$C_4$alkyl, or is oxy or thio, $alk_1$ is $C_2$–$C_4$alkylene, $R_2$ is $C_1$–$C_3$alkyl or hydrogen and $alk_2$ is ethylene, or a pharmaceutically acceptable salt thereof.

7. A compound as claimed in claim 1 being 3-[N-(3-Phenoxypropyl)-N-methylamino]-1-hydroxypropane-1,1-diphosphonic acid or a pharmaceutically acceptable salt thereof.

8. A compound as claimed in claim 1 being 3-{N-[2-(4-Methoxyphenoxy)-ethyl]-amino}-1-hydroxypropane-1,1-diphosphonic acid or a pharmaceutically acceptable salt thereof.

9. A compound as claimed in claim 1 being 3-[N-(2-Phenoxyethyl)-N-methylamino]-1-hydroxypropane-1,1-diphosphonic acid or a pharmaceutically acceptable salt thereof.

10. A compound as claimed in claim 1 being 3-[N-(2-Phenylthioethyl)-N-methylamino]-1-hydroxypropane-1,1-diphosphonic acid or a pharmaceutically acceptable salt thereof.

11. A compound as claimed in claim 1 being 3-[N-(3-Phenoxypropyl)amino]-1-hydroxypropane-1,1-diphosphonic acid or a pharmaceutically acceptable salt thereof.

12. A compound as claimed in claim 1 being 3-[N-(3-Phenylthiopropyl)-N-methylamino]-1-hydroxypropane-1,1-diphosphonic acid or a pharmaceutically acceptable salt thereof.

13. A compound as claimed in claim 1 being 3-{N-[3-(4-Chlorophenoxy)propyl]-N-methylamino-1-hydroxypropane-1,1-diphosphonic acid or a salt thereof.

14. A compound as claimed in claim 1 being 3-[N-(3-(4-Methoxyphenoxy)propylamino]-1-hydroxypropane-1,1-diphosphonic acid or a pharmaceutically acceptable salt thereof.

15. A compound as claimed in claim 1 being 3-[N-(4-(Phenylthiobutyl)-N-methylamino]-1-hydroxypropane-1,1-diphosphonic acid or a pharmaceutically acceptable salt thereof.

16. A compound as claimed in claim 1 being 3-{N-[2-(3-Trifluoromethylphenylamino)-ethyl]-N-methylamino}-1-hydroxypropane-1,1-diphosphonic acid or a pharmaceutically acceptable salt thereof.

17. A compound as claimed in claim 1 being 3-{N-[3-(2-Pyridylamino)-propyl]-N-methylamino}-1-hydroxypropane-1,1-diphosphonic acid or a pharmaceutically acceptable salt thereof.

18. A compound as claimed in claim 1 being 3-{N-[3-(2-Pyrimidinyl)-propyl]-N-methylamino}-1-hydroxypropane-1,1-diphosphonic acid or a pharmaceutically acceptable salt thereof.

19. A compound as claimed in claim 1 being 3-[N-(3-Benzosulfonyl)-ethyl]-N-methylamino]-1-hydroxypropane-1,1-diphosphonic acid or a pharmaceutically acceptable salt thereof.

20. A compound as claimed in claim 1 being 3-{N-[3-(4-Methoxyphenoxy)-propyl]-N-methylamino}-1-hydroxypropane-1,1-diphosphonic acid or a pharmaceutically acceptable salt thereof.

21. A compound as claimed in claim 1 being 3-{N-[3-(3-Methylphenoxy)-propyl]-N-methylamino}-1-hydroxypropane-1,1-diphosphonic acid or a pharmaceutically acceptable salt thereof.

22. A compound as claimed in claim 1 being 3-{N-[3-(4-Fluorophenoxy)-propyl]-N-methylamino}-1-hydroxypropane-1,1-diphosphonic acid or a pharmaceutically acceptable salt thereof.

23. A compound as claimed in claim 1 being 3-[N-(4-(Phenoxybutyl)-N-methylamino]-1-hydroxypropane-1,1-diphosphonic acid or a pharmaceutically acceptable salt thereof.

24. A compound as claimed in claim 1 being 3-[N-(6-(Phenoxyhexyl)-N-methylamino]-1-hydroxypropane-1,1-diphosphonic acid or a pharmaceutically acceptable salt thereof.

25. A compound as claimed in claim 1 being 3-{N-[2-(4-Chlorophenoxy)-ethyl]-N-methylamino}-1-hydroxypropane-1,1-diphosphonic acid or a pharmaceutically acceptable salt thereof.

26. A compound as claimed in claim 1 being 3-{{N-{3-[N'-(Pyrid-2-yl)-N'-ethylamino]-propyl}-N-ethylamino}}-1-hydroxypropane-1,1-diphosphonic acid or a pharmaceutically acceptable salt thereof.

27. A compound as claimed in claim 1 being 3-{N-[2-(2-Hydroxyphenoxy)-ethyl]-N-methylamino}-1-hydroxypropane-1,1-diphosphonic acid or a pharmaceutically acceptable salt thereof.

28. A pharmaceutical formulation containing an effective amount of a compound according to claim 1 or a pharmaceutically acceptable salt thereof for the regulation of calcium metabolism in warm-blooded animals together with customary pharmaceutical adjuncts and excipients.

29. Method of treatment of inflammatory processes of the joints, degenerative processes in articular cartilage, osteoporosis, periodontitis, hyperparathyroidism and calcium deposits in blood vessels and prosthetic implants comprising administering a compound according to claim 1 or a pharmaceutically acceptable salt thereof to a warm-blooded animal in need of such treatment.

* * * * *